(12) United States Patent
Ryu et al.

(10) Patent No.: US 8,324,238 B2
(45) Date of Patent: Dec. 4, 2012

(54) ASPARTATE OF 1-CYCLOPROPYL-6-FLUORO-7-(8-METHOXYIMINO-2,6-DIAZA-SPIRO[3.4]OCT-6-YL)-4-OXO-1,4-DIHYDRO-[1,8]NAPHTHYRIDINE-3-CARBOXYLIC ACID, METHOD FOR PREPARING THE SAME, AND ANTIMICROBIAL PHARMACEUTICAL COMPOSITION COMPRISING THE SAME

(75) Inventors: Jei Man Ryu, Anyang-si (KR); Dong Rack Choi, Yongin-si (KR); Jin Yang, Seoul (KR); Sue Hye Yoon, Suwon-si (KR); Seung Hwan Kim, Uiwang-si (KR); Sae Kwang Ku, Suwon-si (KR)

(73) Assignee: Dong Wha Pharmaceutical Co. Ltd., Seoul (KR)

( * ) Notice: Subject to any disclaimer, the term of this patent is extended or adjusted under 35 U.S.C. 154(b) by 335 days.

(21) Appl. No.: 12/595,606

(22) PCT Filed: Apr. 14, 2008

(86) PCT No.: PCT/KR2008/002106
§ 371 (c)(1),
(2), (4) Date: Mar. 23, 2010

(87) PCT Pub. No.: WO2008/127060
PCT Pub. Date: Oct. 23, 2008

(65) Prior Publication Data
US 2010/0184795 A1    Jul. 22, 2010

(30) Foreign Application Priority Data
Apr. 13, 2007    (KR) .................. 10-2007-0036574

(51) Int. Cl.
*A01N 43/42* (2006.01)
*A61K 31/44* (2006.01)
*C07D 471/02* (2006.01)

(52) U.S. Cl. ........... 514/300; 514/278; 546/15; 546/123

(58) Field of Classification Search ................. 514/278, 514/300; 546/15, 123
See application file for complete search history.

(56) References Cited

U.S. PATENT DOCUMENTS

| 4,957,922 A | * | 9/1990 | Lammens et al. | ....... 514/253.08 |
| 5,563,149 A | * | 10/1996 | Jung et al. | ..................... 514/300 |
| 6,552,196 B2 | * | 4/2003 | Yoon et al. | ..................... 546/15 |

FOREIGN PATENT DOCUMENTS

| EP | 0 067 666 A1 | 12/1982 |
| JP | 2006-182784 A | 7/2006 |
| WO | 99/00393 | 1/1999 |
| WO | 01/24803 A2 | 4/2001 |

OTHER PUBLICATIONS

Han et al., "Subacute Toxicity and Toxicokinetics of a New Antibiotic, DW-224a, after Single and 4-Week Repeated Oral Administration in Dogs," *Biol. Pharm. Bull.* 26(6):832-839, 2003.
Kosowska-Shick et al., "Antipneumococcal Activity of DW-224a, a New Quinolone, Compared to Those of Eight Other Agents," *Antimicrobial Agents and Chemotherapy* 50(6):2064-2071, 2006.
Kwon et al., "*In vitro* and *in vivo* activities of DW-224a, a novel fluoroquinolone antibiotic agent," *Journal of Antimicrobial Chemotherapy* 58:684-688, 2006.
Park et al., "In Vitro and In Vivo Antibacterial Activities of DW-224a, a New Fluoronaphthyridone," *Antimicrobial Agents and Chemotherapy* 50(6):2261-2264, 2006.
English translation of Japanese Office Action, issued Oct. 2, 2012, for Japanese Patent Application No. 2010-502952, 4 pages.

* cited by examiner

*Primary Examiner* — D M Seaman
*Assistant Examiner* — Niloofar Rahmani
(74) *Attorney, Agent, or Firm* — Seed IP Law Group PLLC

(57) ABSTRACT

Disclosed are aspartic acid salts of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, methods for preparing the same, and antimicrobial pharmaceutical compositions comprising the same.

10 Claims, No Drawings

ASPARTATE OF 1-CYCLOPROPYL-6-FLUORO-7-(8-METHOXYIMINO-2,6-DIAZA-SPIRO[3.4]OCT-6-YL)-4-OXO-1,4-DIHYDRO-[1,8]NAPHTHYRIDINE-3-CARBOXYLIC ACID, METHOD FOR PREPARING THE SAME, AND ANTIMICROBIAL PHARMACEUTICAL COMPOSITION COMPRISING THE SAME

CROSS-REFERENCE TO RELATED APPLICATIONS

This application is a U.S. national stage application filed under 35 U.S.C. §371 of International Patent Application No. PCT/KR2008/002106, accorded an international filing date of Apr. 14, 2008, which claims priority to Republic of Korea (KR) Patent Application No. 10-2007-0036574 filed Apr. 13, 2007 all of which applications are incorporated herein by reference in their entirety.

TECHNICAL FIELD

Disclosed are aspartic acid salts of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, methods for preparing the same, and anti-microbial pharmaceutical compositions comprising the same.

BACKGROUND ART

Background of the Invention

Quinolone carboxylic acid derivatives are synthetic antimicrobial agents, and are widely effective in the treatment of infectious diseases of human or animals. Currently, quinolone antimicrobial agents such as ciprofloxacin, norfloxacin, and ofloxacin, are employed in the treatment of human diseases. These agents are very active against gram negative bacteria. However, problems exist where these agents show moderate or weak activity against gram positive bacteria. Various studies have been made to determine limitations of several known quinolone antimicrobial agents. Sparfloxacin is a representative example of an improved antimicrobial agent that is active against gram positive bacteria. However, this compound shows weak activity against methicillin resistant *Staphylococcus aureus* (MRSA) and gradually increases numbers of quinolone resistant strains, in addition to streptococci.

DISCLOSURE OF INVENTION

Technical Problem

The above mentioned bacteria strains are well known to be pathogens responsible for causing respiratory infections. Thus, improved quinolone antimicrobial agents are needed, especially against these pathogens.

Technical Solution

SUMMARY OF THE INVENTION

In one aspect are aspartic acid salts or aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid represented by Formula (I):

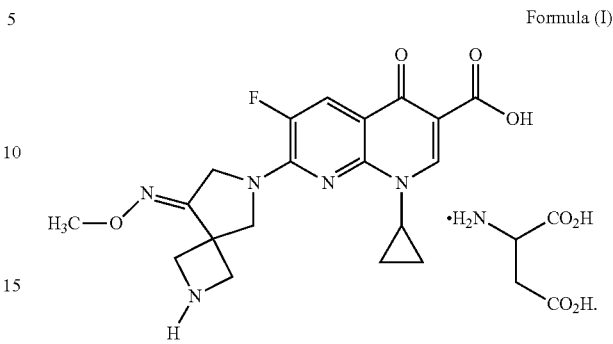

Formula (I)

In some embodiments of this aspect, the aspartic acid is selected from D-aspartic acid, L-aspartic acid, DL-aspartic acid or a non-racemic mixture of D-aspartic acid and L-aspartic acid. In some embodiments, the aspartic acid is D-aspartic acid.

In another aspect are pharmaceutically acceptable aspartic acid salts of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid represented by Formula (I):

Formula (I)

In some embodiments of this aspect, the aspartic acid is selected from D-aspartic acid, L-aspartic acid, DL-aspartic acid, or a non-racemic mixture of D-aspartic acid and L-aspartic acid. In some embodiments, the aspartic acid is D-aspartic acid.

In another aspect are methods for preparing the aspartic acid salt or aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, comprising reacting 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid with aspartic acid in a solvent.

In some embodiments of this aspect, the solvent is at least one selected from the group consisting of ethyl acetate, methanol, ethanol, isopropanol, acetone, acetonitrile, hexane, isopropyl ether, and water. In some embodiments of this aspect, the solvent is selected from the group consisting of ethyl acetate, methanol, ethanol, isopropanol, acetone, acetonitrile, hexane, isopropyl ether, water, and any combination thereof. In some embodiments, the solvent is ethanol.

In some embodiments of this aspect, the aspartic acid is selected from D-aspartic acid, L-aspartic acid, DL-aspartic acid, or a non-racemic mixture of D-aspartic acid and L-aspartic acid.

In some embodiments of this aspect, the yield of preparing the aspartic acid salts of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid is at least 70%. In some embodiments, the yield is at least 80%. In some embodiments, the yield is at least 85%. In some embodiments, the yield is at least 90%.

In some embodiments of this aspect, the yield of preparing the aspartic acid salts of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid is between about 70% and about 80%. In some embodiments, the yield is between about 75% and about 85%. In some embodiments, the yield is between about 85% and about 95%. In some embodiments, the yield is between about 90% and about 99%.

In another aspect are antimicrobial pharmaceutical compositions comprising an aspartic acid salt or aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid.

In some embodiments of this aspect, the aspartic acid is selected from D-aspartic acid, L-aspartic acid, DL-aspartic acid or a non-racemic mixture of D-aspartic acid and L-aspartic acid. In some embodiments, the aspartic acid is D-aspartic acid.

In some embodiments of this aspect, the composition is formulated for injection. In some embodiments, the composition comprises an injection formulation.

In another aspect are methods of treating a disease or condition in an animal using a therapeutically effective amount of at least one pharmaceutically acceptable aspartic acid salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid represented by Formula (I):

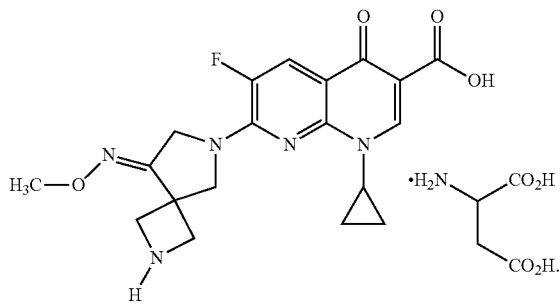

Formula (I)

In some embodiments of this aspect, the aspartic acid is selected from D-aspartic acid, L-aspartic acid, DL-aspartic acid, or a non-racemic mixture of D-aspartic acid and L-aspartic acid. In some embodiments, the aspartic acid is D-aspartic acid.

In another aspect is the use of a compound of Formula (I), in the manufacture of a medicament for treating a disease or condition in an animal.

In some embodiments of this aspect, the aspartic acid is selected from D-aspartic acid, L-aspartic acid, DL-aspartic acid, or a non-racemic mixture of D-aspartic acid and L-aspartic acid. In some embodiments, the aspartic acid is D-aspartic acid.

In another aspect are compounds of Formula (I) for use in a method of treating a disease or condition in an animal.

In some embodiments of this aspect, the aspartic acid is selected from D-aspartic acid, L-aspartic acid, DL-aspartic acid, or a non-racemic mixture of D-aspartic acid and L-aspartic acid. In some embodiments, the aspartic acid is D-aspartic acid.

INCORPORATION BY REFERENCE

All publications and patent applications mentioned in this specification are herein incorporated by reference to the same extent as if each individual publication or patent application was specifically and individually indicated to be incorporated by reference.

BEST MODE FOR CARRYING OUT THE INVENTION

Detailed Description of the Invention

Disclosed are aspartic acid salts or aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid. Also disclosed are methods for preparing aspartic acid salts or aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid. Also disclosed are antimicrobial pharmaceutical compositions comprising an aspartic acid salt or aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid.

Glossary of Terms

Unless otherwise stated, the following terms used in this application, including the specification and claims, have the definitions given below. It must be noted that, as used in the specification and the appended claims, the singular forms "a", "an", and "the" include plural referents unless the context clearly dictates otherwise. Definition of standard chemistry terms may be found in reference works, including Carey and Sundberg, *Advanced Organic Chemistry* 4$^{th}$ *Ed.*, Vols. A (2000) and B (2001), Plenum Press, New York, N.Y. Unless otherwise indicated, conventional methods of mass spectroscopy, NMR, HPLC, protein chemistry, biochemistry, recombinant DNA techniques and pharmacology, within the skill of the art are employed.

As used in the present specification, the following words and phrases are generally intended to have the meanings as set forth below, except to the extent that the context in which they are used indicates otherwise.

The terms "optional" or "optionally" as used herein, alone or in combination, mean that the subsequently described event or circumstance may or may not occur, but need not occur, and that the description includes instances where the event or circumstance occurs and instances in which it does not.

The term "protecting group" as used herein, refers to a chemical moiety which blocks some, or all, reactive moieties and prevents such groups from participating in chemical reactions until the protective group is removed. The procedures and specific groups involved are known to those of skill in the art and can readily be found in reference sources such as Greene and Wuts, Protective Groups in Organic Synthesis, 3$^{rd}$ Ed. (1999) John Wiley & Sons, New York, N.Y., which is incorporated herein by reference in its entirety.

Where chemical groups are specified by their conventional chemical formulas, written from left to right, they equally encompass the chemically identical substituents that would result from writing the structure from right to left; for example, —CH$_2$O— is equivalent to —OCH$_2$—.

The term "pharmaceutical agent" refers to any agent which imparts or is intended to impart a therapeutic effect and is used or indicated for use as a pharmaceutical. Pharmaceutical agents may be used in the treatment, diagnosis, modulation, or prevention of a diseased state or symptom thereof. One of skill in the art is able to select appropriate pharmaceutical agents when addressing a particular disease or symptom. Exemplary pharmaceutical agents contemplated within the scope of the invention are provided in the following references (the disclosures of all of which are hereby incorporated by reference): Lippincott et al., *Remington's Pharmaceutical Sciences: The Science and Practice of Pharmacy*, 20th Ed., Williams and Wilkins Publishing, Baltimore (2000); and Lewis et al., *Hawley's Condensed Chemical Dictionary*, 14th Ed., John Wiley Publishing, New York (2001).

The term "acceptable" with respect to a formulation, composition or ingredient, as used herein, means having no persistent detrimental effect on the general health of the subject being treated.

The term "pharmaceutically acceptable" as used herein, alone or in combination, refers to a material which does not abrogate the biological activity or properties of the compound, and is relatively nontoxic. Thus, a pharmaceutically acceptable component (such as a salt, carrier, excipient or diluent) of a pharmaceutical agent delivery composition containing compounds of Formula (I) should be (1) compatible with the other ingredients of the delivery composition to deliver the pharmaceutical agent; and (2) where the delivery composition is intended for therapeutic use with an animal (e.g. a human) should not provoke undue adverse side effects, such as toxicity, irritation and allergic response. Side effects are undue when their risk outweighs the benefit provided by the pharmaceutical agent, i.e., the material may be administered to an individual without causing undesirable biological effects or interacting in a deleterious manner with any of the components of the composition in which it is contained.

The term "pharmaceutically acceptable salt" of a compound, as used herein, refers to a salt that is pharmaceutically acceptable. A pharmaceutically acceptable salt is a salt which retains the biological effectiveness and properties of the compounds and which are not biologically or otherwise undesirable. In some cases, the compounds of Formula (I) are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "prodrug" as used herein, refers to a drug or compound in which metabolic processes within the body convert the drug or compound into a pharmacologically active form.

The term "pharmaceutical combination" as used herein, means a product that results from the mixing or combining of more than one active ingredient and includes both fixed and non-fixed combinations of the active ingredients. The term "fixed combination" means that the active ingredients, e.g. at least one compound of Formula (I) and a co-agent, are both administered to a patient simultaneously, in the form of a single entity or dosage. The term "non-fixed combination" means that the active ingredients, e.g. at least one compound of Formula (I) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "effective amount" or "therapeutically effective amount" as used herein, refer to a sufficient amount of an agent or compound being administered which will relieve to some extent one or more of the symptoms of the disease or condition being treated, when administered to a mammal in need of such treatment. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. The therapeutically effective amount will vary depending upon the subject and disease condition being treated, the weight and age of the subject, the severity of the disease condition, the particular compound, the dosing regimen to be followed, timing of administration, the manner of administration and the like, all of which can readily be determined by one of ordinary skill in the art. An appropriate effective amount in any individual case may be determined using techniques, such as a dose escalation study.

The term "excipient" refers to a generally pharmaceutically inactive or inert substance used as a diluent or vehicle for a drug. Different forms of drug administration may require a different excipient and a "pharmaceutically acceptable excipient" includes a "pharmaceutically acceptable carrier". For example, tablets, troches, pills, capsules, and the like, may contain expicients including a binder such as gum tragacanth, acacia, corn starch or gelatin; a disintegrating agent such as corn starch, potato starch, alginic acid; a lubricant such as magnesium stearate; a sweetening agent such as sucrose, lactose or saccharin; and/or a flavoring agent such as peppermint, oil or wintergreen or cherry flavoring. Capsules may contain additional expicient such as a liquid carrier. Syrups or elixirs may contain expicients including a sweetening agent such as sucrose, a preservative such as methyl and propylparabens, a dye and/or flavoring such as cherry or orange flavor.

The terms "enhance" or "enhancing" as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount" as used herein, refers to an amount adequate to enhance the effect of another therapeutic agent in a desired system.

The term "modulate" or "modulating" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist and an antagonist.

The terms "co-administration" and the like, as used herein, are meant to encompass administration of the selected therapeutic agents to a single patient, and are intended to include treatment regimens in which the agents are administered by the same or different route of administration or at the same or different time.

The term "pharmaceutical composition" as used herein, refers to a mixture of an active compound with other chemical components, such as carriers, stabilizers, diluents, dispersing agents, suspending agents, thickening agents, and/or excipients.

The terms "carrier", "pharmaceutically acceptable carrier", or "pharmaceutically acceptable excipient" as used herein, refer to relatively nontoxic chemical compounds or agents that facilitate the incorporation of a compound into cells or tissues. They include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat", "treating", or "treatment" as used herein, include at least partially alleviating, abating or ameliorating a disease or condition symptoms, at least partially preventing additional symptoms, ameliorating or preventing the underlying metabolic causes of symptoms, at least partially inhibiting the disease or condition, e.g., arresting the development of the disease or condition, at least partially relieving the disease or condition, at least partially causing regression of the disease or condition, at least partially relieving a condition caused by the disease or condition, or at least partially stopping the symptoms of the disease or condition. Thus any treatment of a disease in a mammal should provide at least a partial therapeutic or prophylactic effect, including any, all or a combination of the following:

a) preventing the onset of disease, that is, causing the clinical symptoms of the disease not to develop;

b) delaying the onset of disease, that is, causing the clinical symptoms of the disease to develop at a later time;

c) reducing the severity of the onset of disease, that is causing the clinical symptoms of the disease to develop less severely;

d) relieving an ongoing disease, that is, causing the regression of clinical symptoms;

e) arresting an ongoing disease, that is, causing the elimination of clinical symptoms; and/or f) enhancing normal physiological functioning.

Compounds of Formula (I) can be prepared as pharmaceutically acceptable salts formed when an acidic proton present in the parent compound either is replaced by a metal ion, for example an alkali metal ion, an alkaline earth ion, or an aluminum ion; or coordinates with an organic base. In addition, the salt forms of the disclosed compounds can be prepared using salts of the starting materials or intermediates.

Compounds of Formula (I) can be prepared as pharmaceutically acceptable acid addition salts (which are a type of pharmaceutically acceptable salt) by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Alternatively, compounds of Formula (I) can be prepared as pharmaceutically acceptable base addition salts (which are a type of a pharmaceutically acceptable salt) by reacting the free acid form of the compound with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds of Formula (I) can be conveniently prepared or formed during the processes described herein. By way of example only, hydrates of compounds of Formula (I) can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Compounds of Formula (I) include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds of Formula (I) can be prepared as prodrugs. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of Formula (I) which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See for example Fedorak et al, *Am. J. Physiol.* (1995) 269, G210-218; McLoed et al, *Gastroenterol* (1994) 106, 405-413; Hochhaus et al, *Biomed. Chrom*, (1992) 6, 283-286; Larsen and Bundgaard, *Int. J. Pharmaceutics* (1987) 37, 87; Larsen et al, *Int. J. Pharmaceutics* (1988) 47, 103; Sinkula et al, *J. Pharm. Sci.* (1975) 64, 181-210; Higuchi and Stella, *Prodrugs as Novel Delivery Systems*, Vol. 14 of the A.C.S. Symposium Series; and Roche, *Bioreversible Carriers in Drug Design* (1987) American Pharmaceutical Association and Pergamon Press, all incorporated herein in their entirety.

Additionally, prodrug derivatives of compounds of Formula (I) can be prepared by methods known to those of ordinary skill in the art (for further details see for example Saulnier et al, *Bioorg. and Med. Chem. Lett.* (1994)4, p. 1985). By way of example only, appropriate prodrugs can be prepared by reacting a non-derivatized compound of Formula (I) with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized invivo to produce a derivative as set forth herein are included within the scope of the claims. Indeed, some of the herein-described compounds may be a prodrug for another derivative or active compound.

In other embodiments, the compounds described herein may be labeled isotopically (e.g. with a radioisotope) or by another other means, including, but not limited to, the use of chromophores or fluorescent moieties, bioluminescent labels, or chemiluminescent labels. The compounds of Formula (I) may possess one or more chiral centers and each center may exist in the R or S configuration. The compounds presented herein include all diastereomeric, enantiomeric, and epimeric forms as well as the appropriate mixtures thereof. Compounds of Formula (I) can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds described herein, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jacques, Collet and Wilen, *Enantiomers, Racemates and Resolutions* (1981) John Wiley & Sons, New York, N.Y., herein incorporated by reference in its entirety.

Additionally, the compounds and methods provided herein may exist as geometric isomers. The compounds and methods provided herein include all cis, trans, syn, anti, entgegen (E), and zusammen (Z) isomers as well as the appropriate mixtures thereof. In some situations, compounds may exist as tautomers. All tautomers are included within the formulas described herein are provided by compounds and methods herein. In additional embodiments of the compounds and methods provided herein, mixtures of enantiomers and/or diastereoisomers, resulting from a single preparative step, combination, or interconversion may also be useful for the applications described herein.

1-Cyclopropyl-6-fluoro-7-(8-methoxyimino-2,6-diaza-spiro[3.4]oct-6-yl)-4-oxo-1,4-dihydro-[1,8]naphthyridine-3-carboxylic acid shows excellent antimicrobial activity against gram positive bacteria, gram negative bacteria, methicillin resistant bacteria, penicillin resistant bacteria, and the known quinolone resistant strains among quinolone antimicrobial agents. However, the aqueous solubility of this agent is low (See Korean Patent No. 10-566346).

Generally, it is desirable that an active ingredient used in a pharmaceutical composition has high solubility in water or in aqueous solution over a wide range of pH values. To increase the pharmaceutical utility of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, a salt form of this compound having excellent solubility was developed.

Various salt forms of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid are disclosed in Korean Patent No. 10-566346. Examples of the salt forms disclosed include an inorganic acid such as hydrochloric acid, phosphoric acid and sulfuric acid; an organic acid such as methanesulfonic acid, p-toluenesulfonic acid, acetic acid, citric acid, maleic acid, succinic acid, oxalic acid, benzoic acid, tartaric acid, fumaric acid, mandelic acid, glucuronic acid; and a cation such as sodium ion, and potassium ion. Phosphate and hydrochloride salt forms of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid were thought to have the best solubility among the salts of the above acids.

Hydrochloride salt form of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid causes severe fibrous peritonitis and therefore not suitable for injection formulation.

Aspartic acid (2-aminosuccinic) is a stable, naturally occurring amino acid and has no moisture absorption or corrosive characteristics, thus allowing it to be handled with safety. Since aspartic acid is also readily available in quantity, it can be easily used in large scale production. In addition, aspartic acid has been approved by the United States Food and Drug Administration for use as a food additive or a pharmaceutical component.

Aspartic acid protects the liver from some drug toxicity, aids mineral absorption, and improves the functions of DNA, RNA, and immune system.

It has been found that aspartic acid salts or aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid can have much higher solubility, excellent physical properties such as stability, and importantly, displays substantially no toxicity, as compared to the phosphate and hydrochloride salt forms. In some embodiments, aspartic acid salts or aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid can cause less severe fibrous peritonitis as compared to the hydrochloride salt form. In some embodiments, aspartic acid salts or aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid can show higher lethal dose (LD) as compared to the hydrochloride salt form. In some embodiments, aspartic acid salts or aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid can show higher lethal dose (LD) as compared to the phosphate salt form.

In one aspect, provided are aspartic acid salt forms of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid represented by the structure of Formula (I).

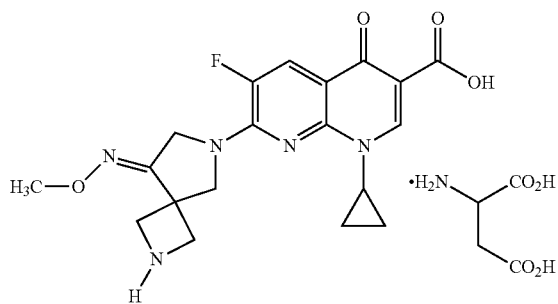

Formula (I)

In a further or alternative embodiment, the aspartic acid is D-aspartic acid. In a further or alternative embodiment, the aspartic acid is L-aspartic acid. In a further or alternative embodiment, the aspartic acid is DL-aspartic acid or a racemic mixture thereof. In yet another further or alternative embodiment, the aspartic acid is a non-racemic mixture of D-aspartic acid and L-aspartic acid.

The aspartic acid salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid has better solubility than 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, or a hydrochloride salt thereof and/or the phosphate salt thereof.

In some embodiments, the solubility of the aspartic acid salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid is about 4 to about 8 times more than that of the hydrochloride in distilled water. In some embodiments, the solubility of the aspartic acid salt is about 5 to about 6 times more than that of the hydrochloride in distilled water.

In some embodiments, the solubility of the aspartic acid salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid is about 15 to about 30 times more than that of the hydrochloride in aqueous solution with a pH of 1.2. In some embodiments, the solubility of the aspartic acid salt is about 17 to about 27 times more than that of the hydrochloride in aqueous solution with a pH of 1.2. In some embodiments, the solubility of the aspartic acid salt is about 25 to about 30 times more than that of the hydrochloride in aqueous solution with a pH of 1.2.

In some embodiments, the solubility of the aspartic acid salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid is and about 50 to about 150 times more than that of the hydrochloride in aqueous solution with a pH of 6.8. In some embodiments, the solubility of the aspartic acid salt is about 69 to 130 times more than that of the hydrochloride in aqueous solution with a pH of 6.8. In some embodiments, the solubility of the aspartic acid salt is about 80 to 120 times more than that of the hydrochloride in aqueous solution with a pH of 6.8.

In some embodiments, the aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid is stable at room temperature. In some embodiments, the aspartate is more stable than the hydrochloride salt form. In some embodiments, the aspartate is more stable than the phosphate salt form.

In some embodiments, the aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid has the highest median lethal dose, as compared to other salts (methanesulfonate, hydrochloride, phosphate, or formate) when dosed intraparenteral.

In some embodiments, the aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid has the highest approximate lethal dose, as compared to other salts (methanesulfonate, hydrochloride, phosphate, or formate) when dosed intraparenteral.

In one embodiment, the aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid may be a crystalline form. In another embodiment, the aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid may be a noncrystalline form.

In another aspect, provided are methods for preparing the aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid of Formula (I).

In some embodiments, the method for preparing the aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid comprises a step of reacting 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid with aspartic acid in a solvent. The method can be represented by Scheme 1.

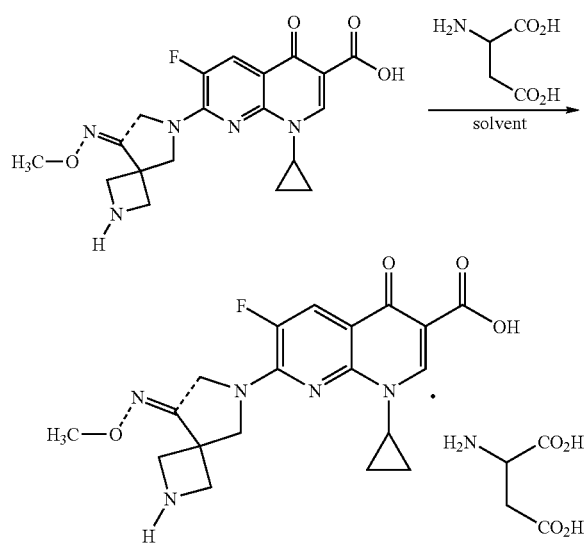

1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid can be dissolved in an inactive organic solvent. The inactive organic solvent can be used in 10 to 20 fold volume (ml) to the weight (g) of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid. Aspartic acid can be added thereto with from 0.9 to 2.5 equivalent weight, based on 1 equivalent weight of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid. In some embodiments, Aspartic acid can be added from 1.0 to 1.5 equivalent weight. The reaction of Scheme 1 can be carried out at temperature of 30 to 70° C. In some embodiments, the reaction of Scheme 1 is carried out at temperature of 40 to 60° C. The reaction of Scheme 1 can last from 10 minutes to 5 hours. In some embodiments, the reaction of Scheme 1 lasts from 30 minutes to 2 hours.

In one embodiment for the preparation of the aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, the aspartic acid is D-aspartic acid. In a further or alternative embodiment, the aspartic acid is L-aspartic acid. In a further or alternative embodiment, the aspartic acid is DL-aspartic acid or a racemic mixture thereof. In yet another further or alternative embodiment, the aspartic acid is a non-racemic mixture of D-aspartic acid and L-aspartic acid.

In some embodiments of the method for the preparation of the aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, the solvent is selected from the group consisting of ethyl acetate, methanol, ethanol, isopropanol, acetone, acetonitrile, hexane, isopropyl ether, water, and any combination thereof. In some embodiments, the solvent is ethanol.

In another aspect, provided are antimicrobial pharmaceutical compositions comprising the aspartic acid salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid of Formula (I). In some embodiments, the aspartic acid is selected from D-aspartic acid, L-aspartic acid, DL-aspartic acid or a non-racemic mixture of D-aspartic acid and L-aspartic acid.

For administration, the antimicrobial pharmaceutical composition can be prepared including at least one pharmaceutically acceptable carrier, in addition to the active ingredients as described above. Examples of the pharmaceutically acceptable carrier include saline solution, sterile water, Ringer's solution, buffered saline solution, dextrose solution, maltodextrin solution, glycerol, ethanol and a mixture of two or more thereof. If necessary, the composition may also contain other conventional additives, such as antioxidants, buffers, and bacteriostatic agents. Moreover, the composition may additionally contain diluents, dispersants, surfactants, binders, and lubricants in order to formulate it into injectable formulations, such as aqueous solution, suspension, and emulsion, pills, capsules, granules and tablets. Furthermore, the composition may be formulated depending on particular diseases and its components, using methods described in Remington's Pharmaceutical Science, Mack Publishing Company, Easton Pa.

The composition of this aspect can be administered orally or parenterally (for example, intravenous, subcutaneous, intraperitoneal, or topical application). The dosage of the composition of the invention can vary depending on various factors, including patient's weight, age, sex, health condition and diet, and administration time, administration route, secretion rate, disease severity, etc. In some embodiments, the aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid of Formula (I) can be administered at a daily dosage of about 1 to 100 mg/kg, preferably 2 to 20 mg/kg, one time or several times per day.

The composition of the invention can be used alone or in combination with other therapeutic agents. In some embodiments, the composition is in combination with at least one other antimicrobial agent.

Pharmaceutical Composition/Formulation/Administration

A pharmaceutical composition, as used herein, refers to a mixture of at least one compound Formula (I) with other chemical components, such as carriers, stabilizers, diluents, dispersing agents, suspending agents, thickening agents, and/or excipients. The pharmaceutical composition facilitates administration of the compound to an organism. Pharmaceutical compositions containing at least one compound of Formula (I) can be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, otic, nasal, and topical administration.

One may administer pharmaceutical compositions in a local rather than systemic manner, for example, via injection of the compound directly into an organ, often in a depot or sustained release formulation. Furthermore, one may administer pharmaceutical compositions containing at least one compound of Formula (I) in a targeted drug delivery system, for example, in a liposome coated with organ-specific antibody. The liposomes will be targeted to and taken up selectively by the organ. In addition, pharmaceutical compositions containing at least one compound of Formula (I) may be provided in the form of rapid release formulations, in the form of extended release formulations, or in the form of intermediate release formulations.

For oral administration, compounds of Formula (I) can readily be formulated by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a patient to be treated.

Pharmaceutical preparations for oral use can be obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner. Parental injections may involve for bolus injection or continuous infusion. The pharmaceutical compositions of Formula (I) may be in a form suitable for parenteral injection as sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredients may be in powder form for constitution with a suitable vehicle, e.g., sterile pyrogen-free water, before use.

The compounds of Formula (I) can be administered topically and can be formulated into a variety of topically administrable compositions, such as solutions, suspensions, lotions, gels, pastes, medicated sticks, balms, creams or ointments. Such pharmaceutical compositions can contain solubilizers, stabilizers, tonicity enhancing agents, buffers and preservatives.

Formulations suitable for transdermal administration of the compounds of Formula (I) may employ transdermal delivery devices or transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds of Formula (I) can be accomplished by means of iontophoretic patches and the like. Additionally, transdermal patches can provide controlled delivery of the compounds of Formula (I). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

For administration by inhalation, the compounds of Formula (I) may be in a form such as an aerosol, a mist or a powder. Pharmaceutical compositions comprising at least one compound of Formula (I) can be conveniently delivered in the form of an aerosol spray presentation from pressurized packs or nebulisers, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, such as, by way of example only, gelatin for use in an inhaler or insufflator may be formulated containing a powder mix of the compound and a suitable powder base such as lactose or starch.

The compounds of Formula (I) may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In practicing the methods of treatment or use provided herein, therapeutically effective amounts of compounds of Formula (I) provided herein are administered in pharmaceutical compositions to a mammal having a disease or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. Pharmaceutical compositions comprising at least one compound of Formula (I) may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one pharmaceutically acceptable carrier, diluent or excipient and at least one compound of Formula (I) as described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein. In addition, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

A summary of pharmaceutical compositions described herein may be found, for example, in Remington, *The Science and Practice of Pharmacy*, 19$^{th}$Ed. (1995) Mack Publishing Company, Easton, Pa.; Hoover, *Remington's Pharmaceutical Sciences* (1975) Mack Publishing Company, Easton, Pa.; Liberman and Lachman, *Pharmaceutical Dosage Forms* (1980) Marcel Decker, New York, N.Y.; and Lippincott, Williams & Wilkins, *Pharmaceutical Dosage Forms and Drug Delivery Systems, 7th Ed.* (1999) all of which are herein incorporated by reference in their entirety.

The compounds according to the disclosure are effective over a wide dosage range. For example, in the treatment of adult humans, dosages from about 0.01 to about 10,000 mg, from about 0.5 to about 1000 mg, from about 1 to about 500 mg per day, and from about 5 to about 100 mg per day are examples of dosages that in some embodiments are used. The exact dosage will depend upon the route of administration, the form in which the compound is administered, the subject to be treated, the body weight of the subject to be treated, and the preference and experience of the attending physician.

Mode for the Invention

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

1-Cyclopropyl-6-fluoro-7-(8-methoxyimino-2,6-diaza-spiro[3.4]oct-6-yl)-4-oxo-1,4-dihydro-[1,8]naphthyridine-3-carboxylic acid can be prepared by the same method described in Korean Patent No. 10-566346. A methanesulfonate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid can be prepared by the same method as described in Korean Patent No. 10-566346.

EXAMPLE 1

Preparation of the D-Aspartic Acid Salt of 1-cyclopropyl-6-fluoro-7-(8-methoxyimino-2,6-diaza-spiro [3.4]oct-6-yl)-4-oxo-1,4-dihydro-[1,8]naphthyridine-3-carboxylic acid 1-Cyclopropyl-6-fluoro-7-(8-methoxyimino-2,6-diaza-spiro[3.4]oct-6-yl)-4-oxo-1,4-dihydro-[1,8]naphthyridine-3-carboxylic acid (5.0 g) was added to 50% ethanol (80 mL), and then the mixture was stirred at 50° C. for 10 minutes. D-Aspartic acid (2.0 g) was added and then the mixture was stirred at 50° C. for 1 hour. The mixture was cooled to room temperature, and then the resulting solid was collected by filtration. Ethanol (100 mL) was added to the filtrate, and then the mixture was stirred for 30 minutes. The resulting solid was collected by filtration to obtain a total of 5.55 g of the target compound (yield: 83%). Melting point: 200-201° C. $^1$H NMR (D$_2$O): δ 0.97 (bs, 2H), 1.27 (d, 2H), 2.00 (dd, 1H, J=8.8, 17.6 Hz), 2.77 (dd, 1H, J=3.3, 17.0 Hz), 3.53 (bs, 1H), 3.84 (dd, 1H, J=3.3, 8.78 Hz), 4.01 (s, 3H), 4.31-4.45 (m, 8H), 7.46 (d, 1H, J=12.2 Hz), 8.42 (s, 1H).

EXAMPLE 2

Preparation of L-Aspartic Acid Salt of 1-cyclopropyl-6-fluoro-7-(8-methoxyimino-2,6-diaza-spiro[3.4] oct-6-yl)-4-oxo-1,4-dihydro-[1,8]naphthyridine-3-carboxylic acid 1-Cyclopropyl-6-fluoro-7-(8-methoxyimino-2,6-diaza-spiro[3.4]oct-6-yl)-4-oxo-1,4-dihydro-[1,8]naphthyridine- 3-carboxylic acid (500 mg) was added to 50% ethanol (20 mL), and then the mixture was stirred at 50° C. for 10 minutes. L-Aspartic acid (174 mg) was added and then the mixture was stirred at 50° C. for 1 hour. The mixture was cooled to room temperature. Ethanol (20 mL) was added to the reaction mixture, and then the mixture was stirred for 30 minutes. The resulting solid was collected by filtration to obtain 550 mg of the target compound (yield: 82%). Melting point: 205-206° C. $^1$H NMR ($d_6$-DMSO): δ 0.93 (d, 2H, J=3.5 Hz), 1.20 (d, 2H, J=6.8 Hz), 2.42 (dd, 1H, J=9.2, 17.3 Hz), 2.59 (dd, 1H, J=3.3, 17.2 Hz), 3.50 (m, 1H), 3.59 (1H, dd, J=3.1, 9.1 Hz), 3.91 (s, 3H), 4.24 (m, 6H), 4.41 (br, 2H), 7.59 (d, 1H, J=12.4 Hz), 8.41 (s, 1H).

EXAMPLE 3

Preparation of Hydrochloric Acid Salt, Phosphate Salt, and Formate Salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid

3-1 Hydrochloric Acid Salt

Ethanol (3 mL) was cooled to 0° C. and acetyl chloride (1.13 mL) was added, and then the mixture was stirred for 30 minutes. 1-Cyclopropyl-6-fluoro-7-(8-methoxyimino-2,6-diaza-spiro[3.4]oct-6-yl)-4-oxo-1,4-dihydro-[1,8]naphthyridine-3-carboxylic acid (800 mg) was added to the reaction mixture, and then stirred at 0° C. for 30 minutes. Tetrahydrofuran (4 mL) was added, and then the mixture was stirred for 30 minutes. The resulting solid was collected by filtration and dried to obtain 776 mg of the target compound (yield: 89%). Melting point: 244-245° C. $^1$H NMR ($d_6$-DMSO): δ 1.07 (d, 2H, J=4.7 Hz), 1.21 (d, 2H, J=6.8 Hz), 3.68 (m, 1H), 3.94 (s, 3H), 4.17 (m, 2H), 4.40 (s, 2H), 4.53 (s, 2H), 8.03 (d, 1H, J=12.5 Hz), 8.59 (s, 1H).

3-2 Phosphate Salt

1-Cyclopropyl-6-fluoro-7-(8-methoxyimino-2,6-diaza-spiro[3.4]oct-6-yl)-4-oxo-1,4-dihydro-[1,8]naphthyridine-3-carboxylic acid (5.0 g) is added to 50% ethanol (180 mL), and then the mixture was stirred at 50° C. for 10 minutes. Phosphoric acid (0.84 mL) was added, and then the mixture was stirred at 50° C. for 1 hour. The mixture was cooled to room temperature. The resulting solid was collected by filtration and dried to obtain 3.8 g of the target compound (yield: 61%). Melting point: 220-222° C. $^1$H NMR ($d_6$-DMSO): δ 1.11 (d, 2H, J=4.2 Hz), 1.21 (d, 2H, J=7.6 Hz), 3.71 (m, 1H), 3.97 (s, 3H), 4.18 (m, 4H), 4.41 (m, 2H), 4.55 (m, 2H), 8.06 (d, 1H, J=12.6 Hz), 8.59 (s, 1H).

3-3 Formate Salt

1-Cyclopropyl-6-fluoro-7-(8-methoxyimino-2,6-diaza-spiro[3.4]oct-6-yl)-4-oxo-1,4-dihydro-[1,8]naphthyridine-3-carboxylic acid (5.0 g) was dissolved in ethanol (50 mL), and then 85% formic acid (0.5 mL) was added. The mixture was stirred at 50° C. for 2 hours, and then stirred again at room temperature for 3 hours. The resulting solid was collected by filtration and dried to obtain 4.07 g of the target compound (yield: 73%). Melting point: 198-199° C. $^1$H NMR ($d_6$-DMSO): δ 1.10 (d, 2H, J=2.4 Hz), 1.25 (d, 2H, J=6.6 Hz), 3.72 (m, 1H), 3.98 (m, 5H), 4.09 (m, 2H), 4.39 (s, 2H), 4.55 (s, 2H), 8.04 (d, 1H, J=12.6 Hz), 8.31 (s, 1H), 8.58 (s, 1H).

EXAMPLE 4A

Solubility Determination of Various Salt Forms

Solubility of the parent compound, solubility of the hydrochloride salt, solubility of the D-aspartic acid salt, and solubility of the L-aspartic acid salt are measured under the conditions of various solvents at room temperature. The results are shown in Table 1.

TABLE 1

Table 1 - Solubility of Various Salt Forms

| | Salt Form Solubility (mg/mL) | | | |
|---|---|---|---|---|
| | Parent Compound | Hydrochloride (Example 3) | D-Aspartate (Example 1) | L-Aspartate (Example 2) |
| Distilled water | 2.22 | 13.5 | 63.5 | 77.9 |
| pH 1.2 | 7.70 | 1.62 | 44.2 | 28.3 |
| pH 4.0 | 6.49 | 8.96 | 76.1 | 56.2 |
| pH 6.8 | 0.038 | 0.061 | 7.92 | 4.21 | shown in Table 1, the D-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, and the L-aspartate of 1-cyclopropyl-6-fluoro-7-(8-methoxy-imino-2,6-diaza-spiro[3.4]oct-6-yl)-4-oxo-1,4-dihydro-[1,8]naphthyridine-3-carboxylic acid have greater solubility than 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, or the hydrochloride thereof.

The solubility of the D-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, and the solubility of the L-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid can be about 5 to 6 times more than that of hydrochloride in distilled water, about 17 to 27 times more than that of hydrochloride with a pH of 1.2, and/or about 69 to 130 times more than that of hydrochloride with a pH of 6.8.

EXAMPLE 4B

Solubility Determination of Various Salt Forms

The solubilities of the D-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid and the L-aspartate of 1-cyclopropyl-6-fluoro-7-(8-methoxy-imino-2,6-diaza-spiro[3.4]oct-6-yl)-4-oxo-1,4-dihydro-[1,8]naphthyridine-3-carboxylic acid prepared as described above and various salts of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid in distilled water were measured at room temperature.

The results are shown in the table below, in which the solubilities were converted into the corresponding solubilities of free base (mg/ml).

| Salt | Solubility (mg/ml) |
|---|---|
| Free base | 2.22 |
| (D)-Aspartate | 59.02 |
| (L)-Aspartate | 49.59 |
| Hydrochloride | 17.18 |
| Phosphate | 19.62 |
| Formate | 38.84 |
| Malonate | 5.26 |
| Phthalate | 0.48 |

-continued

| Salt | Solubility (mg/ml) |
| --- | --- |
| Oxalate | 2.26 |
| Nitrate | 2.19 |
| Arginine | 0.09 |
| Maleate | 0.18 |
| Magnesium | 0.02 |
| Acetate | 0.02 |
| Malate | 0.91 |
| Salicylate | 0.11 |
| Hydrobromide | 7.27 |
| Benzoate | 0.67 |
| p-Toluenesulfate | 0.74 |
| Succinate | 2.50 |
| Fumarate | 0.63 |
| Tartarate | 2.80 |
| Mandelate | 1.01 |
| Sulfate | 2.79 |
| 2,5-Dihydroxybenzoate | 0 |

As shown above, the D-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid, and the L-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid of the present invention showed the best solubility.

EXAMPLE 5

Stability Determination of D-aspartic Acid Salt 30 mg of D-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid as prepared in Example 1 is dissolved in 100 ml of distilled water, and then subjected to stability test at room temperature. The results are shown in Table 2.

TABLE 2

Table 2 - Stability of D-Aspartic acid salt

| Time Course | Content (%) |
| --- | --- |
| Initial | 99.32 |
| After 1 week | 99.16 |
| After 2 weeks | 99.04 |

As shown in Table 2, the D-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid does not change its purity at room temperature over the time course of the experiment. Therefore, its chemical stability is found to be well suited for injectable formulation.

EXAMPLE 6

Mouse Toxicity Test

Toxicity profile of the D-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid is confirmed in male ICR mice. Male ICR mice are divided into six dose groups (five mice per group), and then fasted (no food is given except water) for 24 hours. The D-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid (as prepared in Example 1) and other salt forms (including methanesulfonate, hydrochloride, phosphate, and formate), are administrated intraperitoneally at a daily dose of 2000, 1000, 500, 250, 125, and 0 (control) mg/kg administered (10 ml/kg total injection volume) one time per day. A median lethal dose (LD50), an approximate lethal dose, and a maximum tolerate dose are determined after observation for 14 days.

Mortality, body weight changes, and organ weight changes are measured. Necropsy and histopathology findings are also performed. All mice in the 2000 mg/kg group and 2 mice in the 1000 mg/kg group die within two hours after treatment. One mouse in the 1000 mg/kg group dies eight days after treatment. Diarrhea and/or soft feces can be detected in some mice. Increased weights in spleen, testis, or epididymis can be detected in some mice. Immature germ cells in the lumen of testicular tubules can be detected in the 500 mg/kg group. Some mice show infiltration of inflammatory cells in the attached fibrous tissues of spleen or necrotic foci around the fibrous tissue attached regions in the liver. The results of toxicity are shown in Table 3.

TABLE 3

Table 3 - Mouse Toxicity Determination

| Salt Form | Median lethal dose (mg/kg) | Approximate lethal dose (mg/kg) | Maximum tolerate dose (mg/kg) |
| --- | --- | --- | --- |
| D-Aspartate (Example 1) | 963.13 | 500-1000 | 500 |
| Methanesulfonate | 716.24 | 500-1000 | 500 |
| Hydrochloride (Example 3) | 481.93 | 250-500 | 250 |
| Phosphate (Example 3) | 356.91 | 250-500 | 250 |
| Formate (Example 3) | 716.24 | 500-1000 | 500 |

As shown in Table 3, it is found that the D-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid has the highest median lethal dose and highest approximate lethal dose, as compared to other salt forms (including methanesulfonate, hydrochloride, phosphate, and formate). Accordingly, it can be concluded that the D-aspartate of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid has substantially reduced toxicity.

EXAMPLE 7

Preparation of an Injectable Formulation

An injectable formulation containing 10 mg/mL of the active ingredient is prepared by the following method:

1 g of the compound of Formula (I), 0.6 g of sodium chloride, and 0.1 g of ascorbic acid are dissolved in distilled water and the final volume made to be 100 mL.

EXAMPLE 8

Two-weeks Repeated Intravenous Toxicity Study in Beagle Dogs 14-month old Male Beagle dogs (11.80 13.80 kg; Gaoyao Kangda Laboratory Animal Science & Technology Co., LTD., China) are administered intravenously once daily at dose levels of 10, 5, 2.5, 1, and 0 (control) mg/kg (body wt.) for 2 weeks. The mortality and changes on body weight, clinical signs and gross observation are monitored during the 14 days with organ weight and histopathology of 23 types of principle organs.

D-aspartic acid salt form of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid (Example 1) is homogeneously suspended in distilled water at 200 mg/ml concentration, and is well dissolved at 40, 20, 10, and 4 mg/ml concentrations. The test article is two-weeks repeated intravenously injected at a dosage volume of 0.25 ml/kg using distill water as vehicle.

No mortality is observed in all experimental groups including vehicle control group.

ClinicalXobserved during the experiment are vomiting and salivation. Vomiting is observed except for the control group. Salivation is observed in the 5 and 10 mg/kg dosing groups. Restlessness, diarrhea, injection site swelling, are sporadically observed in the 5 or 10 mg/kg dosing groups.

No significant body weight changes are observed.

No significant organ weight changes are observed.

EXAMPLE 9

Pharmacokinetics in Mice

Seven week old male mice (ICR CD-1), 28-31 g of body weight upon receipt, are used. For each of the 100 mg/kg study and 10 mg/kg study, a total of seventy-two mice are divided into eighteen groups nine groups for the hydrochloride salt form (Example 3) and nine groups for the D-aspartate salt form (Example 1).

Blood is sampled at 0.25, 0.5, 1, 1.5, 2, 3, 4, and 5 hours after dosing by orbital puncture. Pharmacokinetics of the hydrochloride salt form (Example 3) and the D-aspartate salt form (Example 1) are compared in mice as shown in Table 4.

TABLE 4

Table 4 - Pharmacokinetics in Mice

| PK parameters* | 100 mg/kg, p.o. | | 10 mg/kg, i.v. | |
| --- | --- | --- | --- | --- |
| | Hydrochloride (Example 3) | D-Aspartate (Example 1) | Hydrochloride (Example 3) | D-Aspartate (Example 1) |
| C max (µg/mL) | 3.951 | 3.412 | — | — |
| T max (hr) | 0.25 | 0.25 | — | — |
| C last (µg/mL) | — | — | 0.067 | 0.092 |
| T last (hr) | — | — | 4.0 | 4.0 |
| Half-life (hr) | 2.205 | 1.707 | 1.259 | 1.543 |
| AUC 0-8 hr (µg × hr/mL) | 8.963 | 8.679 | 2.140 | 1.907 |
| Total AUC (µg × hr/mL) | 9.653 | 9.051 | 2.310 | 2.112 |

*Only mean parameters shown.

EXAMPLE 10

Pharmacokinetic Study after Intravenous Administration in Rats

Pharmacokinetics of the hydrochloride salt form (Example 3) and the D-aspartate salt form (Example 1) are compared in rats as shown in Table 5.

TABLE 5

Table 5 - Pharmacokinetics in Rats (10 mg/kg i.v. in male SD rats)

| PK parameters | Hydrochloride (Example 3) | D-Aspartate (Example 1) |
| --- | --- | --- |
| C last (µg/mL) | 0.137 ± 0.042 | 0.107 ± 0.025 |
| T last (hr) | 5.0 ± 0.0 | 5.0 ± 0.0 |
| Half-life (hr) | 1.061 ± 0.093 | 1.058 ± 0.040 |
| AUC 0-5 hr | 6.070 ± 0.731 | 5.228 ± 0.615 |
| AUC inf (µg × hr/mL) | 6.283 ± 0.804 | 5.393 ± 0.650 |

EXAMPLE 11

Pharmacokinetics in Dogs

Four male beagle dogs are purchased from Gaoyao Kangda Laboratory Animal Sciences & Technology Co., LTD. The dose is formulated as a solution in sterile water at a concentration of 5 mg/0.1 ml/kg of body weight. The D-aspartate salt form (Example 1) is administered intravenously via a cephalic vein.

Blood samples are collected via the cephalic vein into tubes containing sodium heparin anticoagulant and at 0.083, 0.25, 0.5, 1, 1.5, 2, 3, 5, and 8 hours post-administration. Pharmacokinetic parameters are calculated using WinNonlin (ver 1.0, Scientific Consulting Inc., USA). Pharmacokinetics of the D-aspartate salt form (Example 1) are shown in Table 6.

TABLE 6

Table 6 - Pharmacokinetics in Dogs (5 mg/kg i.v.)

| Parameters | Dog A | Dog B | Dog C | Dog D | Mean ± SD |
| --- | --- | --- | --- | --- | --- |
| C last (µg/mL) | 0.369 | 0.412 | 0.380 | 0.387 | 0.387 ± 0.018 |
| T last (hr) | 8 | 8 | 8 | 8 | 8 ± 0 |
| Half-life (hr) | 3.38 | 4.12 | 3.51 | 4.00 | 3.75 ± 0.37 |
| AUC 0-8 hr (µg × hr/mL) | 7.293 | 7.345 | 7.535 | 6.650 | 7.206 ± 0.385 |
| AUC inf (µg × hr/mL) | 9.092 | 9.795 | 9.457 | 8.886 | 9.307 ± 0.402 |
| CL (ml/min/kg) | 9.2 | 8.5 | 8.8 | 9.4 | 9.0 ± 0.4 |
| Varea (L/kg) | 2.7 | 3.0 | 2.7 | 3.3 | 2.9 ± 0.3 |
| MRT (hr) | 4.74 | 5.68 | 4.90 | 5.65 | 5.24 ± 0.49 |

EXAMPLE 12

Single Dose Toxicity in Mice and Rats

For mice study, single dose intravenous injections of the D-aspartate salt form (Example 1) are carried out with the following dosages: 900, 400, 200, 100, and 50 mg/kg/10 ml. 10 ml/kg distilled water is used as control. Mortality, body weight changes, and organ weight changes are measured. Histopathology findings are also performed.

All mice in the 900 and 400 mg/kg group die after the end of the treatment. The 200, 100, and 50 mg/kg groups show no serious toxicity. No significant target organ is found.

For rat study, single dose intravenous injections of the D-aspartate salt form (Example 1) are carried out with the following dosages: 600, 300, 150, 75, 37.5 mg/kg/5 ml. 5 ml/kg distilled water is used as control. Mortality, body weight changes, and organ weight changes are measured. Histopathology findings are also performed.

All rats in the 600 and 300 mg/kg group die after the end of the treatment. Loss of locomotion can be detected in the 150 and 75 mg/kg groups. Slight body weight increase can be observed in the 150 and 75 mg/kg groups. Also organ weight increase can be observed for liver and thymus in the 150 and 75 mg/kg groups.

Results of single dose toxicity are shown in Table 7.

TABLE 7

Table 7 - IV Toxicity Determination in Mice and Rats

|  | 50% lethal dose ($LD_{50}$) mg/kg | Approximate lethal dose (ALD) mg/kg |
|---|---|---|
| Mice | 279.98 | 200-400 |
| Rats | 210.72 | 150-300 |

EXAMPLE 13

Intravenous Bolus Injection Toxicity Study

Once a day two-weeks repeated dose toxicity experiments of the D-aspartate salt form (Example 1) are carried out similarly as Example 8 in both dogs and rats. Results of i.v. repeated single dose toxicity are shown in Table 8.

TABLE 8

Table 8 - IV Toxicity Determination in Dogs and Rats

| Animal |  | Maximum tolerate dose mg/kg |
|---|---|---|
| Rats | Male | 80 |
|  | Female | 40 |
| Dogs | Male | 10 |

EXAMPLE 14

Micronucleus Test in Bone Marrow Cells of Male Mice

Bone marrow cytogenetics is a useful short-term technique for elucidating the mechanism as well as to identify substances clastogenic and anticlastogenic activity. See Renner H W, (1990) *Mutat Res.* 244: 185-8. The micronucleus test using small rodents can be sensitive methods for testing the genotoxicity of newly developed agents.

The D-aspartate salt form (Example 1) or cyclophosphamide (CPA) is used for this experiment. Experimental intravenous high dosage is 250 mg/kg and low dosage is 200 mg/kg for the D-aspartate salt form (Example 1). 70 mg/kg intraperitoneally administration of CPA is used as a positive control dosage (seven male ICR mice are used in each group). Twenty-four hours after single injection administration, all animals are sacrificed and the changes on the number of polychromatic erythrocyte with one or more nuclei (MN-PCE) are evaluated with the changes on the total white blood cells and difference counts on the neutrophils and lymphocytes on the prepared blood. In addition, PCE/(PCE+normochromatic erythrocytes (NCE)) ratio are calculated by counting 500 erythrocytes for detecting possibility of cytotoxicity.

Single intravenous injection at 200 or 250 mg/kg can cause death followed by seizures after the end of treatment. For mice survive after the end of treatment, loss of locomotion can be detected within 4 hours after injection. Results of mortality or loss of locomotion are shown in Table 9.

TABLE 9

Table 9 - Results of Mortality or Loss of Locomotion

| Group ID | Mortality | Loss of Locomotion |
|---|---|---|
| Intact Control | 0/7 | 0/7 |
| Positive Control (CPA 70 mg/kg) | 0/7 | 0/7 |
| High dosage (250 mg/kg) | 6/7 | 1/1 |
| Low dosage (200 mg/kg) | 1/7 | 6/6 |

Significant decreases in blood total leukocyte numbers are detected in CPA treated and 200 mg/kg injected groups with dramatic increase in proportions of lymphocyte at differential counts on blood smear. No significant changes on the body weight or MNPCE numbers for all D-aspartate salt form treated groups, where CPA treated group shows significant increase of MNPCE. Thus, the micronucleus test in bone marrow cells of male ICR show negative result for the D-aspartate salt form of 1-cyclopropyl-6-fluoro-7-(8-methoxy-imino-2,6-diaza-spiro[3.4]oct-6-yl)-4-oxo-1,4-dihydro-[1, 8]naphthyridine-3-carboxylic acid. Changes on the MNPCE numbers and PCE(PCE+NCE) ratio are shown in Table 10. Changes on the leukocytes and neutophiles are shown in Table 11.

TABLE 10

Table 10 - Changes on the MNPCE Numbers and PCE(PCE + NCE) Ratio

| Group ID | MNPCEs 2000 PCEs | PCE(PCE + NCE) ratio |
|---|---|---|
| Intact Control | 0.71 ± 0.76 | 0.51 ± 0.07 |
| Positive Control (CPA 70 mg/kg) | 71.86 ± 10.43 | 0.36 ± 0.07 |
| High dosage (250 mg/kg) | 5.00 ± ND* | 0.41 ± ND* |
| Low dosage (200 mg/kg) | 1.00 ± 1.10 | 0.34 ± 0.04 |

*Not calculated because of high mortality

TABLE 11

Table 11 - Changes on the Leukocytes and Neutophiles

| Group ID | Total leukocyte numbers ($\times 10^3$ cells $mm^3$) | Proportions among 100 leukocytes (%) | |
|---|---|---|---|
|  |  | Lymphocytes | Neutrophils |
| Intact Control | 5.02 ± 1.10 | 89.71 ± 4.39 | 9.71 ± 3.73 |
| Positive Control (CPA 70 mg/kg) | 2.36 ± 0.55 | 75.71 ± 9.20 | 21.71 ± 9.45 |
| High dosage (250 mg/kg) | 4.30 ± ND* | 13.00 ± ND* | 82.00 ± ND* |
| Low dosage (200 mg/kg) | 3.20 ± 0.56 | 79.33 ± 5.20 | 17.17 ± 3.19 |

*Not calculated because of high mortality

EXAMPLE 15

Intramuscular Local Irritation Test

For the intramuscular local irritation test, the D-aspartate salt form (Example 1) is repeatedly injected once a day for seven days. Dosages used are 200, 100, and 50 mg/kg. 50 mg/kg ciprofloxacin and 2 ml/kg distilled water (control) are also used. Five mice per group are used.

Various parameters are measured or performed including mortality, clinical signs, changes on body weights, changes on the calf thickness, changes on the organ weights, necropsy findings, changes on the blood WBC counts, and histopathological findings.

TABLE 12

Table 12 - Changes on the Calf Thickness

| Group ID | Intact Calf (A) | Injected Calf (B) | Differences (B – A) |
| --- | --- | --- | --- |
| Control | 4.78 ± 0.08 | 5.22 ± 0.29 | 0.45 ± 0.27 |
| Ciprofloxacin (50 mg/kg) | 4.80 ± 0.07 | 6.00 ± 0.36 | 1.20 ± 0.38 |
| 200 mg/kg dosage | 4.83 ± 0.06 | 6.71 ± 0.19 | 1.88 ± 0.17 |
| 100 mg/kg dosage | 4.78 ± 0.07 | 5.91 ± 0.37 | 1.13 ± 0.43 |
| 50 mg/kg dosage | 4.77 ± 0.12 | 5.13 ± 0.12 | 0.36 ± 0.11 |

Results show that repeated seven-day intramuscular injection of 200 mg/kg the D-aspartate salt form (Example 1) can cause similar local irritation as compared to the same injection of 50 mg/kg ciprofloxacin. Repeated seven-day intramuscular injection of 50 mg/kg the D-aspartate salt form (Example 1) shows only slight local irritations. Changes on the calf thickness are shown in Table 12, and changes on the white blood cell counts are shown in Table 13.

TABLE 13

Table 13 - changes on the white blood cell counts

| Group ID | Total leukocyte numbers (×10³ cells/μl) | Differential counts of leukocytes (%) | | | | |
| --- | --- | --- | --- | --- | --- | --- |
| | | Neutrophils | Lymphocutes | Monocytes | Eosinophils | Basophils |
| Control | 4.57 ± 0.77 | 7.80 ± 2.43 | 87.30 ± 3.40 | 3.60 ± 0.79 | 0.86 ± 1.06 | 0.06 ± 0.09 |
| Ciprofloxacin (50 mg/kg) | 5.51 ± 0.40 | 13.94 ± 4.35 | 80.88 ± 4.29 | 4.58 ± 1.13 | 0.34 ± 0.45 | 0.02 ± 0.04 |
| 200 mg/kg dosage | 5.49 ± 0.21 | 13.84 ± 4.55 | 80.36 ± 4.34 | 5.46 ± 1.14 | 0.04 ± 0.09 | 0.04 ± 0.05 |
| 100 mg/kg dosage | 4.69 ± 0.46 | 8.52 ± 2.04 | 85.28 ± 2.02 | 5.62 ± 1.34 | 0.28 ± 0.41 | 0.06 ± 0.05 |
| 50 mg/kg dosage | 4.50 ± 1.01 | 8.02 ± 1.18 | 86.40 ± 3.07 | 4.64 ± 2.22 | 0.44 ± 0.38 | 0.06 ± 0.05 |

INDUSTRIAL APPLICABILITY

An aspartic acid salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid according to the present invention has excellent physicochemical properties, which include its solubility and stability. Moreover, said acid salt has very low toxicity as shown by its much higher $LD_{50}$ value when compared to other salts. Accordingly, it is very effective for an antimicrobial agent.

The invention claimed is:

1. An aspartic acid salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid represented by Formula (I):

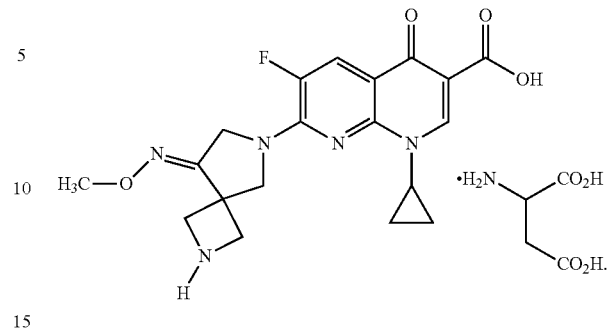

Formula (I)

2. The aspartic acid salt of claim 1, wherein the aspartic acid is selected from D-aspartic acid, L-aspartic acid, DL-aspartic acid or a non-racemic mixture of D-aspartic acid and L-aspartic acid.

3. A method for preparing the aspartic acid salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid of claim 1, comprising a step of reacting 1-cyclopropyl-6-fluoro-7-(8-methoxyimino-2,6-diaza-spiro[3.4]oct-6-yl)-4-oxo-1,4-dihydro-[1,8] naphthyridine-3-carboxylic acid with aspartic acid in a solvent.

4. The method for claim 3, wherein the solvent is at least one selected from the group consisting of ethyl acetate, methanol, ethanol, isopropanol, acetone, acetonitrile, hexane, isopropyl ether, and water.

5. The method of claim 3, wherein the aspartic acid is selected from D-aspartic acid, L-aspartic acid, DL-aspartic acid or a non-racemic mixture of D-aspartic acid and L-aspartic acid.

6. An antimicrobial pharmaceutical composition comprising the aspartic acid salt of 1-cyclopropyl-6-fluoro-7-(8-methoxyimino-2,6-diaza-spiro[3.4]oct-6-yl)-4-oxo-1,4-dihydro-[1,8]naphthyridine-3-carboxylic acid.

7. The composition of claim 6, wherein the aspartic acid is selected from D-aspartic acid, L-aspartic acid, DL-aspartic acid or a non-racemic mixture of D-aspartic acid and L-aspartic acid.

8. The antimicrobial pharmaceutical composition according to claim 6 or 7, wherein the composition is formulated for injection.

9. An pharmaceutically acceptable aspartic acid salt of 1-cyclopropyl-6-fluoro-7-(8-methoxyimino-2,6-diaza-spiro-

[3.4]oct-6-yl)-4-oxo-1,4-dihydro-[1,8]naphthyridine-3-carboxylic acid represented by Formula (I):

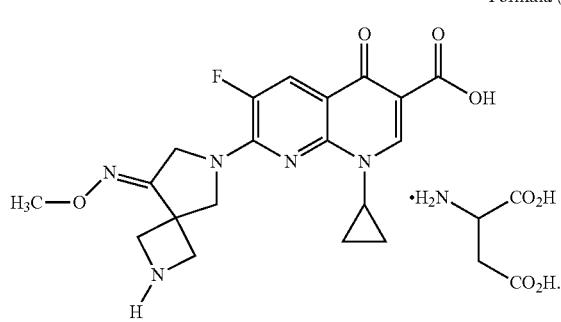

Formula (I)

10. A method of treating bacterial infection in an animal comprising administering to the animal a therapeutically effective amount of at least one pharmaceutically acceptable aspartic acid salt of 1-cyclopropyl-6-fluoro-7-(8-methoxy-imino-2,6-diaza-spiro[3.4]oct-6-yl)-4-oxo-1,4-dihydro-[1,8]naphthyridine-3-carboxylic acid represented by Formula (I):

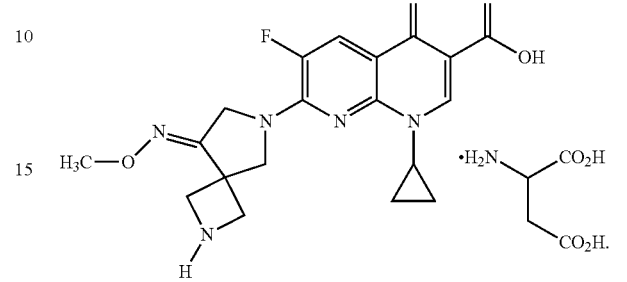

Formula (I)

* * * * *